(12) United States Patent
Duncalf et al.

(10) Patent No.: US 9,060,937 B2
(45) Date of Patent: Jun. 23, 2015

(54) PHARMACEUTICAL COMPOSITIONS

(76) Inventors: David John Duncalf, Wirral (GB); Andrew James Elphick, Oxford (GB); Alison Jayne Foster, Wirral (GB); James Long, Wirral (GB); Steven Paul Rannard, Wirral (GB); Dong Wang, Liverpool (GB)

( * ) Notice: Subject to any disclaimer, the term of this patent is extended or adjusted under 35 U.S.C. 154(b) by 945 days.

(21) Appl. No.: 12/309,292

(22) PCT Filed: Jun. 29, 2007

(86) PCT No.: PCT/EP2007/056564
§ 371 (c)(1),
(2), (4) Date: Jan. 13, 2009

(87) PCT Pub. No.: WO2008/006716
PCT Pub. Date: Jan. 17, 2008

(65) Prior Publication Data
US 2009/0304806 A1    Dec. 10, 2009

(30) Foreign Application Priority Data
Jul. 13, 2006    (GB) ................................. 0613925.7

(51) Int. Cl.
| A61K 9/50 | (2006.01) |
| A61K 9/16 | (2006.01) |
| A61K 31/167 | (2006.01) |
| A01N 25/04 | (2006.01) |
| A61K 9/10 | (2006.01) |
| A61K 9/19 | (2006.01) |

(52) U.S. Cl.
CPC ............. *A61K 9/1617* (2013.01); *A61K 31/167* (2013.01); *A01N 25/04* (2013.01); *A61K 9/10* (2013.01); *A61K 9/1635* (2013.01); *A61K 9/1652* (2013.01); *A61K 9/19* (2013.01)

(58) Field of Classification Search
None
See application file for complete search history.

(56) References Cited

U.S. PATENT DOCUMENTS

| 6,395,300 B1 | 5/2002 | Straub et al. |
| 6,645,528 B1 | 11/2003 | Straub et al. |
| 6,932,983 B1 | 8/2005 | Straub et al. |
| 2002/0041896 A1 | 4/2002 | Straub et al. |
| 2002/0056206 A1* | 5/2002 | Pace et al. ....................... 34/372 |
| 2002/0142050 A1* | 10/2002 | Straub et al. .................. 424/499 |
| 2005/0048116 A1 | 3/2005 | Straub et al. |
| 2005/0058710 A1 | 3/2005 | Straub et al. |
| 2006/0165806 A1* | 7/2006 | Liversidge et al. ............ 424/489 |
| 2008/0152717 A1* | 6/2008 | Doney .......................... 424/489 |

FOREIGN PATENT DOCUMENTS

| WO | 97/13503 | 4/1997 |
| WO | 00/72827 A2 | 12/2000 |
| WO | 2004/028505 | 4/2004 |
| WO | 2004/064834 | 8/2004 |
| WO | 2005/014043 | 2/2005 |
| WO | 2005/072709 | 8/2005 |
| WO | 2006000383 | 1/2006 |
| WO | 2006/074218 A2 | 7/2006 |

OTHER PUBLICATIONS

Pursuant to MPEP § 2001.6(b) applicants bring the following co-pending application to the Examiner's attention: Applicant: Cooper, et al. U.S. Appl. No. 10/587,734, filed May 17, 2007 For: Porous Bodies & Method of Production Thereof.
Pursuant to MPEP § 2001.6(b) applicants bring the following co-pending application to the Examiner's attention: Applicant: Barnwell, et al. U.S. Appl. No. 11/883,215, filed May 27, 2007 For: Spray Dried Composition.
Pursuant to MPEP § 2001.6(b) applicants bring the following co-pending application to the Examiner's attention: Applicant: Cooper, et al. U.S. Appl. No. 11/883,216, filed May 27, 2007 For: Method of Preparing Carrier Liquids.
Pursuant to MPEP § 2001.6(b) applicants bring the following co-pending application to the Examiner's attention: Applicant: Cooper, et al. U.S. Appl. No. 10/587,732, filed May 17, 2007 For: Porous Bodies & Method of Production Thereof.
Pursuant to MPEP § 2001.6(b) applicants bring the following co-pending application to the Examiner's attention: Applicant: Butler, et al. U.S. Appl. No. 10/566,873, filed Jul. 3, 2006 For: Porous Material & Method of Production Thereof.
Pursuant to MPEP § 2001.6(b) applicants bring the following co-pending application to the Examiner's attention: Applicant: Elphick, et al. U.S. Appl. No. 12/309,344, filed Aug. 24, 2009 For: Preparation of Pharmaceutical Compositions.
PCT Search Report, PCT/EP2007/056564, mailed Dec. 21, 2007, 4 pp.
Christensen, et al., "Preparation of Redispersible Dry Emulsions by Spray Drying", International Journal of Pharmaceutics, Amsterdam, NL, vol. 212, No. 2, Jan. 16, 2001, pp. 187-194, XP009055444.

(Continued)

*Primary Examiner* — Snigdha Maewall
(74) *Attorney, Agent, or Firm* — Michael Best & Friedrich LLP

(57) ABSTRACT

A process for the production of a composition comprising a water-insoluble sartan which comprises the steps of: a) providing a mixture comprising: i) a water-insoluble sartan, ii) a water soluble carrier, iii) a solvent for each of the sartan and the carrier, and b) spray-drying the mixture to remove the or each solvent and obtain a substantially solvent-free nano-dispersion of the sartan in the carrier.

10 Claims, No Drawings

(56) References Cited

OTHER PUBLICATIONS

Pursuant to MPEP § 2001.6(b) applicants bring the following co-pending application to the Examiner's attention: Applicant: Duncalf, et al. U.S. Appl. No. 12/309,306 For: Improvements Relating to Nanodispersions.

Pursuant to MPEP § 2001.6(b) applicants bring the following co-pending application to the Examiner's attention: Applicant: Duncalf, et al. U.S. Appl. No. 12/309,295 For: Improvements Relating to Anti-Parasitic Compositions.

Pursuant to MPEP § 2001.6(b) applicants bring the following co-pending application to the Examiner's attention: Applicant: Duncalf, et al. U.S. Appl. No. 12/309,293 For: Improvements Relating to Biocidal Compositions.

Pursuant to MPEP § 2001.6(b) applicants bring the following co-pending application to the Examiners attention: Applicant: Duncalf, et al. U.S. Appl. No. 12/309,294 For: Improvements Relating to Pharmaceutical Compositions.

GB 0613925.7 Great Britain Search Report dated Nov. 13, 2006 (1 page).

* cited by examiner

PHARMACEUTICAL COMPOSITIONS

FIELD OF THE INVENTION

The present invention relates improvements relating to pharmaceutical compositions. In particular it relates to pharmaceutically active compositions and precursors therefor which contain a so-called "sartan"

BACKGROUND OF THE INVENTION

Angiotensin II is formed from Angiotensin I by angiotensin converting enzyme (ACE). Angiotensin II is a component of the renin-angiotensin system. Angiotensin II receptor antagonists block the action of Angiotensin II. The present invention is believed to be generally applicable to hydrophobic Angiotensin II receptor antagonists (sartans) but will be described with particular reference to Valsartan.

Valsartan and other Angiotensin II receptor antagonists (including Candesartan, Eprosartan, Ibresartan, Losartan, Olmesartan and Telmesartan) are primarily used for the treatment of hypertension, and are effective where the patient is intolerant of ACE inhibitor therapy. They do not inhibit the breakdown of kinins and therefore are less frequently associated with the persistent dry cough and/or other side effects that limit ACE inhibitor therapy. More recently, they have been used for the treatment of heart failure in patients intolerant of ACE inhibitor therapy, (particularly candesartan, Irbesartan and losartan). Many Sartans exhibit low water solubility and are practically insoluble in water. This hinders their effective use.

Our co-pending international patent application PCT/GB03/03226 describes the formation of solid, porous beads comprising a three dimensional open-cell lattice of a water-soluble polymeric material. These are typically 'templated' materials formed by the removal of both water and a non-aqueous dispersed phase from a high internal phase emulsion (HIPE) which has a polymer dissolved in the aqueous phase. The beads are formed by dropping the HIPE emulsion into a low temperature fluid such as liquid nitrogen, then freeze-drying the particles formed to remove the bulk of the aqueous phase and the dispersed phase. This leaves behind the polymer in the form of a 'skeletal' structure. The beads dissolve rapidly in water and have the remarkable property that a water-insoluble component dispersed in the dispersed phase of the emulsion prior to freezing and drying can also be dispersed in water on solution of the polymer skeleton of the beads.

WO 2005/011636 discloses a non-emulsion based spray drying process for forming 'solid amorphous dispersions' of drugs in polymers. In this method a polymer and a low-solubility drug are dissolved in a solvent and spray-dried to form dispersions in which the drug is mostly present in an amorphous form rather than in a crystalline form.

Our co-pending applications GB 0501835 and GB 0613925 (filed 13 Jul. 2006) describe how materials which will form a nano-dispersion in water can be prepared, preferably by a spray-drying process. In the first of these applications the water insoluble materials is dissolved in the solvent-phase of an emulsion. In the second, the water-insoluble materials are dissolved in a mixed solvent system and co-exist in the same phase as a water-soluble structuring agent. In both cases the liquid is dried above ambient temperature (above 20 Celsius), such as by spray drying, to produce particles of the structuring agent, as a carrier, with the water-insoluble materials dispersed therein. When these particles are placed in water they dissolve, forming a nano-dispersion of the water-insoluble material with particles typically below 300 nm. This scale is similar to that of virus particles, and the water-insoluble material behaves as though it were in solution.

WO 2006/074218 (Elan Pharma International Ltd) discloses nanoparticulate forms of candesartan (particularly candisartan cilexitil). Particle sizes are disclosed from 2000 nm down to 50 nm. Methods for the production of these nanoparticles include grinding, milling, homogenisation, precipitation and supercritical gas methods.

In the present application the term 'ambient temperature' means 20 degrees Celsius and all percentages are percentages by weight unless otherwise specified.

BRIEF DESCRIPTION OF THE INVENTION

We have now determined that both the emulsion-based and the single-phase method can be used to produce a water-soluble, nano-disperse form of a sartan.

Accordingly, the present invention provides a process for the production of a composition comprising a water-insoluble sartan which comprises the steps of:
a) providing a mixture comprising:
 i) a water-insoluble sartan
 ii) a water soluble carrier,
 iii) a solvent for each of the sartan and the carrier, and
b) spray-drying the mixture to remove the or each solvent and obtain a substantially solvent-free nano-dispersion of the water insoluble sartan in the carrier.

The preferred method of particle sizing for the dispersed products of the present invention employs a dynamic light scattering instrument (Nano S, manufactured by Malvern Instruments UK). Specifically, the Malvern Instruments Nano S uses a red (633 nm) 4 mW Helium-Neon laser to illuminate a standard optical quality UV curvette containing a suspension of material. The particle sizes quoted in this application are those obtained with that apparatus using the standard protocol. Particle sizes in solid products are the particle sizes inferred from the measurement of the particle size obtained by solution of the solid in water and measurement of the particle size Preferably, the peak diameter of the water-insoluble sartan is below 800 nm. More preferably the peak diameter of the water-insoluble sartan is below 500 nm. In a particularly preferred embodiment of the invention the peak diameter of the water-insoluble sartan is below 200 nm, most preferably below 100 nm.

Advantageous compositions obtainable by the process of the present invention comprise a water-insoluble sartan and a water soluble carrier which comprises sartan particles of 40-150 nm average particle size dispersed in the carrier.

It is believed that reduction of the particle size in the eventual nano-dispersion has significant advantages in improving the availability of the otherwise water-insoluble material. This is believed to be particularly advantageous where an improved bio-availability is sought, or, in similar applications where high local concentrations of the material are to be avoided. Moreover it is believed that nano-dispersions with a small particle size are more stable than those with a larger particle size.

In the context of the present invention, "water insoluble" as applied to the sartan means that its solubility in water is less than 10 g/L. Preferably, the water insoluble sartan has solubility in water at ambient temperature (20 Celsius) less than 5 g/L preferably of less than 1 g/L, especially preferably less than 150 mg/L, even more preferably less than 100 mg/L. This solubility level provides the intended interpretation of what is meant by water-insoluble in the present specification.

For example, valsartan has a solubility of 0.18 g/° L and irbesartan has a solubility of <0.1 mg/L.

Preferred water-insoluble sartans include Valsartan, Candesartan, Eprosartan, Irbesartan, Losartan, Olmesartan, Telmesartan and water insoluble derivatives thereof.

Preferred carrier materials are selected from the group consisting of water-soluble inorganic materials, surfactants, polymers and mixtures thereof.

A further aspect of the present invention provides a process for preparing a sartan composition comprising a water-insoluble sartan and a water-soluble carrier, which comprises the steps of:
a) forming an emulsion comprising:
  i) a solution of the sartan in a water-immiscible solvent for the same, and
  ii) an aqueous solution of the carrier, and,
b) drying the solution, to remove water and the water-immiscible solvent to obtain a substantially solvent-free nano-dispersion of the water insoluble sartan in, the carrier For convenience, this class of method is referred to herein as the "emulsion" method.

A further aspect of the present invention provides a process for preparing a sartan composition comprising a water insoluble sartan and a water-soluble carrier which comprises' the steps of:
a) providing a single phase mixture comprising:
  i) at least one non-aqueous solvent
  ii) optionally, water
  iii) a water-soluble carrier material soluble in the mixture of (i) and (ii) and
  iv) a water-insoluble sartan which is soluble in the mixture of (1) and (ii), and,
b) drying the solution to remove water and the water miscible solvent to obtain a substantially solvent-free nano-dispersion of the water insoluble sartan in the carrier.

For convenience, this class of method is referred to herein as the "single-phase" Method.

In the context of the present invention substantially solvent free means' that the free solvent content of the product is less than 15% wt, preferably below 10% wt, more preferably below 5% wt and most preferably below 2% wt.

In the context of the present invention it is essential that both the carrier material and the sartan are essentially fully dissolved in their respective solvents prior to the drying step. It is not within the ambit of the present specification to teach the drying of slurries. For the avoidance of any doubt, it is therefore the case that the solids content of the emulsion or the mixture is such that over 90% wt, preferably over 95%, and more preferably over 98% of the soluble materials present is in solution prior to the drying step.

In relation to the methods mentioned above, the preferred sartan and the preferred carrier materials are as described above and as elaborated on in further detail below. Similarly the preferred physical characteristics of the material are as described above.

The 'single phase' method where both the sartan and the carrier material are dissolved in a phase comprising at least one other non-aqueous solvent (and optional water) is preferred. This is believed to be more efficacious in obtaining a smaller particle size for the nano-disperse sartan. Preferably, the drying step simultaneously removes both the water and other solvents and, more preferably, drying is accomplished by spray drying at above ambient temperature.

The products obtainable by the process aspects Of the present invention are suitable for use in the preparation of medicaments for treatment or prophylaxis of hypertensive diseases.

A further aspect of the present invention provides a method for the preparation of a medicament for use in the treatment hypertensive disease of which comprises the step of preparing a composition according to the present invention.

DETAILED DESCRIPTION OF THE INVENTION

Various preferred features and embodiments of the present invention are described in further detail below.

Sartans:

As noted above the preferred water-insoluble sartans are drugs selected from the group consisting of Valsartan, Candesartan, Eprosartan, Irbesartan, Losartan, Olmesartan, Telmesartan and derivatives and mixtures thereof. These can be present as the sole pharmaceutically active ingredient in compositions according to the present invention or be together with other drugs to provide a so-called 'combination therapy'.

As an illustrative example, Irbesartan is also available in a combination formulation with a low dose thiazide diuretic, invariably hydrochlorothiazide, to achieve an additive anti-hypertensive effect. Irbesartan/hydrochlorothiazide combination preparations are marketed under similar trade names to irbesartan preparations, including CoAprovel, Karvezide, Avalide and Avapro HCT.

Water-Dispersible Product Form:

The present invention provides a method for obtaining a water-dispersible form of an otherwise water-insoluble material. This is prepared by forming a not wholly aqueous intermediate emulsion or solution in which both a water-soluble carrier material and the water insoluble sartan are dissolved. On removal of solvents the insoluble sartan is left dispersed through the water-soluble carrier material. Suitable carrier materials are described in further detail below.

The structure of the material obtained after the drying step is not well understood. It is believed that the resulting dry materials are not encapsulates, as discrete macroscopic bodies of the water-insoluble materials are not present in the dry product. Neither are the dry materials 'dry emulsions' as little or none of the volatile solvent comprising the 'oil' phase of the emulsion remains after the drying step. On addition of water to the dry product the emulsion is not reformed, as it would be with a 'dry emulsion'. It is also believed that the compositions are not so-called solid solutions, as with the present invention the ratios of components present can be varied without loss of the benefits. Also from X-ray and DSC studies, it is believed that the compositions of the invention are not solid solutions, but comprise nano-scale, phase-separated mixtures.

Preferably, the compositions produced after the drying step will comprise the sartan and the carrier in a weight ratio of from 1:500 to 1:1 (as sartan:carrier), 1:100 to 1:1 being preferred. Typical levels of around 10-30% wt water-insoluble sartan and 90-70% wt carrier can be obtained by spray drying.

By the method of the present invention the particle size of the sartan materials can be reduced to below 100 nm and may be reduced to around 15 nm. Preferred particle sizes are in the range 40-15 nm.

'Emulsion' Preparation Method:

In one preferred method according to the invention the solvent for the water-insoluble sartanis not miscible with water. On admixture with water it therefore can form an emulsion.

Preferably, the non-aqueous phase comprises from about 10% to about 95% v/v of the emulsion, more preferably from about 20% to about 68% v/v.

The emulsions are typically prepared under conditions which are well known to those skilled in the art, for example, by using a magnetic stirring bar, a homogeniser, or a rotational mechanical stirrer. The emulsions need not be particularly stable, provided that they do not undergo extensive phase separation prior to drying.

Homogenisation using a high-shear mixing device is a particularly preferred way to make an emulsion in which the aqueous phase is the continuous phase. It is believed that this avoidance of coarse emulsion and reduction of the droplet size of the dispersed phase of the emulsion, results in an improved dispersion of the 'payload' material in the dry product.

In a preferred method according to the invention a water-continuous emulsion is prepared with an average dispersed-phase droplet size (using the Malvern peak intensity) of between 500 nm and 5000 nm. We have found that an 'Ultra-Turrux' T25 type laboratory homogenizer (or equivalent) gives a suitable emulsion when operated for more than a minute at above 10,000 rpm.

There is a directional relation between the emulsion droplet size and the size of the particles of the 'payload' material, which can be detected after dispersion of the materials of the invention in aqueous solution. We have determined that an increase in the speed of homogenization for precursor emulsions can decrease final particle size after re-dissolution.

It is believed that the re-dissolved particle size can be reduced by nearly one half when the homogenization speed increased from 13,500 rpm to 21,500 rpm. The homogenization time is also believed to play a role in controlling re-dissolved particle size. The particle size again decreases with increase in the homogenization time, and the particle size distribution become broader at the same time.

Sonication is also a particularly preferred way of reducing the droplet size for emulsion systems. We have found that a Hert Systems Sonicator XL operated at level 10 for two minutes is suitable.

It is believed that ratios of components which decrease the relative concentration of the anti-parasitic to the solvents and/or the carrier give a smaller particle size.

'Single Phase' Preparation Method:

In an alternative method according to the present invention both the carrier and the sartan are soluble in a non-aqueous solvent or a mixture of such a solvent with water. Both here and elsewhere in the specification the non-aqueous solvent can be a mixture of non-aqueous solvents.

In this case the feedstock of the drying step can be a single phase material in which both the water-soluble carrier and the water-insoluble sartan are dissolved. It is also possible for this feedstock to be an emulsion, provided that both the carrier and the sartan are dissolved in the same phase.

The 'single-phase' method is generally believed to give a better nano-dispersion with a smaller particle size than the emulsion method.

It is believed that ratios of components which decrease the relative concentration of the sartan to the solvents and/or the carrier give a smaller particle size.

Drying:

Spray drying is well known to those versed in the art. In the case of the present invention some care must be taken due to the presence of a volatile non-aqueous solvent in the emulsion being dried. In order to reduce the risk of explosion when a flammable solvent is being used, an inert gas, for example nitrogen, can be employed as the drying medium in a so-called closed spray-drying system. The solvent can be recovered and re-used.

We have found that the 'Buchi' B-290 type laboratory spray drying apparatus is suitable.

It is preferable that the drying temperature should be at or above 100 Celsius, preferably above 120 Celsius and most preferably above 140 Celsius. Elevated drying temperatures have been found to give smaller particles in the re-dissolved nano-disperse material.

Carrier Material:

The carrier material is water soluble, which includes the formation of structured aqueous phases as well as true ionic solution of molecularly mono-disperse species. The carrier material preferably comprises an inorganic material, surfactant, a polymer or may be a mixture of two or more of these.

It is envisaged that other non-polymeric, organic, water-soluble materials such as sugars can be used as the carrier. However the carrier materials specifically mentioned herein are preferred.

Suitable carrier materials (referred to herein as 'water soluble carrier materials') include preferred water-soluble polymers, preferred water-soluble surfactants and preferred water-soluble inorganic materials.

Preferred Polymeric Carrier Materials:

Examples of suitable water-soluble polymeric carrier materials include:

(a) natural polymers (for example naturally occurring gums 20 such as guar gum, alginate, locust bean gum or a polysaccharide such as dextran;

(b) cellulose derivatives for example xanthan gum, xyloglucan, cellulose acetate, methylcellulose, methyl-ethylcellulose, hydroxy-ethylcellulose, hydroxy-ethylmethyl-cellulose, hydroxy-propylcellulose, hydroxy-propylmethylcellulose, hydroxy-propylbutylcellulose, ethylhydroxy-ethylcellulose, carboxy-methylcellulose and its salts (eg the sodium salt—SCMC), or carboxy-methylhydroxyethylcellulose and its salts (for example the sodium salt);

(c) homopolymers of or copolymers prepared from two or more monomers selected from: vinyl alcohol, acrylic acid, methacrylic acid, acrylamide, methacrylamide, acrylamide methylpropane sulphonates, aminoalkylacrylates, aminoalkyl-methacrylates, hydroxyethylacrylate, hydroxyethylmethacrylate, vinyl pyrrolidone, vinyl imidazole, vinyl amines, vinyl pyridine, ethyleneglycol and other alkylene glycols, ethylene oxide and other alkylene oxides, ethyleneimine, styrenesulphonates, ethyleneglycolacrylates and ethyleneglycol methacrylate (d) cyclodextrins, for example beta-cyclodextrin (e) mixtures thereof.

When the polymeric material is a copolymer it may be a statistical copolymer (heretofore also known as a random copolymer), a block copolymer, a graft copolymer or a hyperbranched copolymer. Co-monomers other than those listed above may also be included in addition to those listed if their presence does not destroy the water soluble or water dispersible nature of the resulting polymeric material.

Examples of suitable and preferred homopolymers include poly-vinylalcohol, poly-acrylic acid, poly-methacrylic acid, poly-acrylamides (such as poly-N-isopropylacrylamide), poly-methacrylamide; poly-acrylamines, poly-methyl-acrylamines, (such as polydimethylaminoethylmethacrylate and poly-N-morpholinoethylmethacrylate), polyvinylpyrrolidone, poly-styrenesulphonate, polyvinylimidazole, polyvinylpyridine, poly-2-ethyl-oxazoline poly-ethyleneimine and ethoxylated derivatives thereof.

Polyethylene glycol (PEG), polyvinylpyrrolidone (PVP), poly(2-ethyl-2-oxazaline), polyvinyl alcohol (PVA) hydroxypropyl cellulose and hydroxypropyl-methyl cellulose (HPMC) and alginates are preferred polymeric carrier materials.

Preferred Surfactant Carrier Materials:

Where the carrier material is a surfactant, the surfactant may be non-ionic, anionic, cationic, amphoteric or zwitterionic.

Examples of suitable non-ionic surfactants include ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; alkyl polyglycosides.

Examples of suitable anionic surfactants include alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates.

Examples of suitable cationic surfactants include fatty amine salts; fatty diamine salts; quaternary ammonium compounds; phosphonium surfactants; sulfonium surfactants; sulfonxonium surfactants.

Examples of suitable zwitterionic surfactants include N-alkyl derivatives of amino acids (such as glycine, betaine, aminopropionic acid); imidazoline surfactants; amine oxides; amidobetaines.

Mixtures of surfactants may be used. In such mixtures there may be individual components which are liquid, provided that the carrier material overall, is a solid.

Alkoxylated nonionic's (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB) are particularly preferred as surfactant carrier materials.

Preferred Inorganic Carrier Materials:

The carrier material can also be an water-soluble inorganic material which is neither a surfactant nor a polymer. Simple organic salts have been found suitable, particularly in admixture with polymeric and/or surfactant carrier materials as described above. Suitable salts include carbonate, bicarbonates, halides, sulphates, nitrates and acetates, particularly soluble salts of sodium, potassium and magnesium. Preferred materials include, sodium carbonate, sodium bicarbonate and sodium sulphate. These materials have the advantage that they are cheap and physiologically acceptable. They are also relatively inert as well as compatible with many materials found in pharmaceutical products.

Mixtures of carrier materials are advantageous. Preferred mixtures include combinations of surfactants and polymers. Which include at least one of:
a) Polyethylene glycol (PEG), polyvinylpyrrolidone (PVP), hydroxypropyl cellulose and hydroxypropyl-methyl cellulose (HPMC), alginates and, at least one of;
b) Alkoxylated nonionic's (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB)

The carrier material can also be a water-soluble small organic material which is neither a surfactant a polymer nor an inorganic carrier material. Simple organic sugars have been found to be suitable, particularly in admixture with a polymeric and/or surfactant carrier material as described above. Suitable small organic materials include mannitol, polydextrose, xylitol and inulin etc.

Non-aqueous Solvent:

The compositions of the invention comprise a volatile, second non-aqueous solvent. This may either be miscible with the other solvents in pre-mix before drying or, together with those solvents may form an emulsion.

In one alternative form of the invention a single, non-aqueous solvent is employed in which can form a single phase with water in the presence of the sartan and the carrier. Preferred solvents for these embodiments are polar, protic or aprotic solvents. Generally preferred solvents have a dipole moment greater than 1 and a dielectric constant greater than 4.5.

Particularly preferred solvents are selected from the group consisting of haloforms (preferably dichloromethane, chloroform), lower (C1-C10) alcohols (preferably methanol, ethanol, isopropanol, isobutanol), organic acids (preferably formic acid, acetic acid), amides (preferably formamide, N,N-dimethylformamide), nitrites (preferably aceto-nitrile), esters (preferably ethyl acetate) aldehydes and ketones (preferably methyl ethyl ketone, acetone), and other water miscible species comprising hetroatom bond with a suitably large dipole (preferably tetrahydrofuran, dialkylsulphoxide).

Haloforms, lower alcohols, ketones and dialkylsulphoxides are the most preferred solvents.

In another alternative form of the invention the non-aqueous solvent is not miscible with water and forms an emulsion.

The non-aqueous phase of the emulsion is preferably selected from one or more from the following group of volatile organic solvents:
  alkanes, preferably heptane, n-hexane, isooctane, dodecane, decane;
  cyclic hydrocarbons, preferably toluene, xylene, cyclohexane;
  halogenated alkanes, preferably dichloromethane, dichoroethane, trichloromethane (chloroform), fluorotrichloromethane and tetrachloroethane;
  esters preferably ethyl acetate;
  ketones preferably 2-butanone;
  ethers preferably diethyl ether;
  volatile cyclic silicones preferably either linear or cyclomethicones containing from 4 to 6 silicon units. Suitable examples include DC245 and DC345, both of which are available from Dow Corning Inc.

Preferred solvents include dichloromethane, chloroform, ethanol, acetone and dimethyl sulphoxide.

Preferred non-aqueous solvents, whether miscible or not have a boiling point of less than 150 Celsius and, more preferably, have a boiling point of less than 100 Celsius, so as to facilitate drying, particularly spray-drying under practical conditions and without use of specialised equipment. Preferably they are non-flammable, or have a flash point above the temperatures encountered in the method of the invention.

Preferably, the non-aqueous solvent comprises from about 10% to about 95% v/v of any emulsion formed, more preferably from about 20% to about 80% v/v. In the single phase method the level of solvent is preferably 20-100% v/v.

Particularly preferred solvents are alcohols, particularly ethanol and halogenated solvents, more preferably chlorine-containing solvents, most preferably solvents selected from (di- or tri-chloromethane).

Optional Cosurfactant:

In addition to the non-aqueous solvent an optional co-surfactant may be employed in the composition prior to the drying step. We have determined that the addition of a relatively small quantity of a volatile cosurfactant reduced the particle diameter of the material produced. This can have a significant impact on particle volume. For example, reduction from 297 nm to 252 nm corresponds to a particle size reduction of approximately 40%. Thus, the addition of a small quantity of co-surfactant offers a simple and inexpensive method for reducing the particle size of materials according to the present invention without changing the final product formulation.

Preferred co-surfactants are short chain alcohols or amine with a boiling point of <220° C.

Preferred co-surfactants are linear alcohols. Preferred co-surfactants are primary alcohols and amines. Particularly preferred co-surfactants are selected from the group consisting of the 3-6 carbon alcohols. Suitable alcohol co-surfactants include n-propanol, n-butanol, n-pentanol, n-hexanol, hexylamine and mixtures thereof. Preferably the co-surfactant is present in a quantity (by volume) less than the solvent preferably the volume ratio between the solvent and the co-surfactant falls in the range 100:40 to 100:2, more preferably 100:30 to 100:5.

Preferred Spray-Drying Feedstocks:

Typical spray drying feedstocks comprise:
a) a surfactant,
b) at least one lower alcohol,
c) more than 0.1% of at least one water-insoluble sartan dissolved in the feedstock,
d) a polymer, and,
e) optional water Preferred spray-drying feedstocks comprise:
a) at least one non-aqueous solvent selected from dichloromethane, chloroform, ethanol, acetone, and mixtures thereof,
b) a surfactant selected from PEG co-polymer nonionic's (especially the PEG/PPG Pluronic™ materials), alkyl sulphonates (especially SDS), ester surfactants (preferably sorbitan esters of the Span™ and Tween™ types) and cationics (especially cetyltrimethylammonium bromide—CTAB) and mixtures thereof,
c) more than 0.1% of at least one water-insoluble sartan,
d) a polymer selected from Polyethylene glycol (PEG), Polyvinyl alcohol (PVA), polyvinyl-pyrrolidone (PVP), hydroxypropyl cellulose and hydroxypropyl-methyl cellulose (HPMC), alginates and mixtures thereof, and
e) optionally water.

The drying feed-stocks used in the present invention are either emulsions or solutions which preferably do not contain any solid matter and in particular preferably do not contain any undissolved sartan.

It is particularly preferable that the level of the sartan in the composition should be such that the loading in the dried composition is below 40% wt, and more preferably below 30% wt. Such compositions have the advantages of a small particle size and high effectiveness as discussed above.

Water-Dispersed Form:

On admixture of the water-soluble carrier material with water, the carrier dissolves and the water-insoluble sartan is dispersed through the water in sufficiently fine form that it behaves like a soluble material in many respects. The particle size of the water-insoluble materials in the dry product is preferably such that, on solution in water the water-insoluble materials have a particle size of less than 1 micron as determined by the Malvern method described herein. It is believed that there is no significant reduction of particle size for the sartan on dispersion of the solid form in water.

By applying the present invention significant levels of 'water-insoluble' materials can be brought into a state which is largely equivalent to true solution. When the dry product is dissolved in water it is possible to achieve optically clear solutions comprising more than 0.1%, preferably more than 0.5% and more preferably more than 1% of the water-insoluble material.

It is envisaged that the solution form will be a form suitable for administration to a patient either 'as is' or following further dilution. In the alternative, the solution form of embodiments of the invention may be combined with other active materials to yield a medicament suitable for use in combination therapy.

EXAMPLES

In order that the present invention may be further understood and carried forth into practice it is further described below with reference to non-limiting examples.

Examples 1-20

Pre-mixes for spray drying were made up as in table 1 below. The formulations were spray dried using a BUCHI Mini B-290 spray dryer with solids dissolved in 20 ml ethanol and 1 ml water. In all cases a clear solution was obtained which yielded a dry white powder after spray drying with a fixed pump rate of 10% (~3.6 ml/min).

TABLE 1

| Example | Spray Drying Temperature | Tween 80 | Pluronic F127 | PVP k30 | HPC | HPMC | Sartans | PEG 6000 | Particle Size on re-solution |
|---|---|---|---|---|---|---|---|---|---|
| 1 | 100 | 0.2 | 0.1 | 0.2 | 0 | 0.3 | 0.2 | 0 | 162.5 |
| 2 | 100 | 0.1 | 0.1 | 0.3 | 0 | 0.3 | 0.2 | 0 | 130 |
| 3 | 100 | 0.2 | 0.2 | 0.3 | 0.2 | 0 | 0.1 | 0 | 17.52 |
| 4 | 100 | 0.1 | 0.1 | 0.2 | 0.3 | 0 | 0.1 | 0.2 | 48.8 |
| 5 | 100 | 0.1 | 0.2 | 0.2 | 0 | 0.3 | 0.1 | 0.1 | 19.58 |
| 6 | 100 | 0.1 | 0.2 | 0.2 | 0.2 | 0 | 0.3 | 0 | 151.7 |
| 7 | 100 | 0.2 | 0.1 | 0.3 | 0 | 0 | 0.3 | 0.1 | 124.4 |
| 8 | 100 | 0.2 | 0.2 | 0.2 | 0 | 0 | 0.2 | 0.2 | 45.78 |
| 9 | 100 | 0.2 | 0.1 | 0.3 | 0 | 0.1 | 0.1 | 0.2 | 56.95 |
| 10 | 100 | 0.1 | 0.2 | 0.3 | 0 | 0 | 0.2 | 0.2 | 50.22 |
| 11 | 100 | 0.1 | 0.1 | 0.2 | 0 | 0.1 | 0.3 | 0.2 | 145.2 |
| 12 | 160 | 0.2 | 0.2 | 0.3 | 0 | 0 | 0.3 | 0 | 81.18 |
| 13 | 160 | 0.1 | 0.2 | 0.2 | 0.3 | 0 | 0.2 | 0 | 51.02 |
| 14 | 160 | 0.2 | 0.1 | 0.3 | 0.3 | 0 | 0.1 | 0 | 22.12 |
| 15 | 160 | 0.2 | 0.2 | 0.2 | 0 | 0.3 | 0.1 | 0 | 16.32 |
| 16 | 160 | 0.1 | 0.2 | 0.3 | 0 | 0.3 | 0.1 | 0 | 19.09 |

TABLE 1-continued

| Example | Spray Drying Temperature | Tween 80 | Pluronic F127 | PVP k30 | HPC | HPMC | Sartans | PEG 6000 | Particle Size on re-solution |
|---|---|---|---|---|---|---|---|---|---|
| 17 | 160 | 0.1 | 0.1 | 0.2 | 0 | 0.3 | 0.1 | 0.2 | 33.54 |
| 18 | 130 | 0.145 | 0.145 | 0.245 | 0.103 | 0.103 | 0.18 | 0.08 | 74.2 |
| 19 | 130 | 0.145 | 0.145 | 0.245 | 0.103 | 0.103 | 0.18 | 0.08 | 36.64 |
| 20 | 130 | 0.145 | 0.145 | 0.245 | 0.103 | 0.103 | 0.18 | 0.08 | 52.51 |

For each sample (unless stated otherwise), about 10 mg powder was re-dispersed into 10 ml distilled water at room temperature (21.5° C.) to give a 1 mg/ml nano-dispersion for particle size measurements.

A method of particle sizing for the dispersed products of the present invention used in the following examples employs a dynamic light scattering instrument (Nano S, manufactured by Malvern Instruments UK). Specifically, the Malvern Instruments Nano S uses a red (633 nm) 4 mW Helium-Neon laser to illuminate a standard optical quality UV curvette containing a suspension of material.

Example 21

The formulation of example 14 was scaled up to produce more material in order to conduct a dissolution study.

A dose of valsartan (800 mg of the product equivalent to 80 mg of valsartan) was added to a 1000 ml of de-ionised water, incubated at 36° C. and stirred at a constant 50 rpm. Aliquots of the dissolving mixture were removed at various times, filtered through a 1000 nm syringe filter. Equal volumes of the filtered aqueous mixture and ethanol were mixed to form a single phase solution of the dissolved drug and excipients.

The UV absorbance maxima for valsartan in a 50/50 ethanol/water mixture had previously been determined as 204 nm. However, this region of the UV spectrum is very sensitive to small changes in pH leading to large errors in the readings. As such, a wavelength of 257 nm corresponding to a shoulder in the main valsartan absorbance spectra was used to construct a UV calibration graph for active concentration.

The aliquots recovered from the dissolution test were then examined at this wavelength and an active concentration calculated. Rapid initial dissolution was observed upon adding the powder to the dissolution bath, followed by a declining rate that eventually plateaus at a point corresponding to total dissolution. The dispersion obtained was optically clear and stable.

Examples 22-27

Formulations were produced based on a range of excipients, active loadings, and process conditions. The excipients were chosen from hydroxypropyl cellulose (HPC, Mw 80K, Aldrich), polyvinyl pyrrolidone (PVP k30, Aldrich), hydroxypropyl methyl cellulose (HPMC, Mw 10 k, 6 cps, Aldrich), polyethylene glycol (PEG, Mw 6,000, Fluka), Tween 80 (Aldrich), and pluronic F127 (Aldrich).

Active loadings varied from 10 wt % to 30 wt %, and the spray dry temperature varied from 140° C. to 190° C.

Table 2 lists the formulations and spray temperatures.

TABLE 2

Formulations for Irbesartan Nanoparticles

| Exp No | Spray Drying Temperature, ° C. | Irbessartan, w/w | PVP k30, w/w | HPC, w/w | HPMC, w/w | PEG 6000, w/w | Tween 80, w/w | Pluronic F127, w/w | PSD, nm |
|---|---|---|---|---|---|---|---|---|---|
| 22 | 140 | 0.1 | 0.2 | 0.5 | 0.2 | 0 | 0 | 0 | 86 |
| 23 | 140 | 0.1 | 0.2 | 0.2 | 0.5 | 0 | 0 | 0 | 227 |
| 24 | 140 | 0.1 | 0.2 | 0.2 | 0.2 | 0.3 | 0 | 0 | 155 |
| 25 | 190 | 0.1 | 0.2 | 0.5 | 0.2 | 0 | 0 | 0 | 81 |
| 26 | 190 | 0.1 | 0.2 | 0.2 | 0.2 | 0.3 | 0 | 0 | 165 |
| 27 | 190 | 0.3 | 0.2 | 0.3 | 0.2 | 0 | 0 | 0 | 779 |

Further details of these formulations are listed as below:

Example 22

0.10 g Irbesartan, 0.20 g PVP k30, 0.50 g HPC, and 0.20 g HPMC were all dispersed into 25 ml absolute ethanol followed by addition of 25 ml acetone. The suspension was stirred intensively with magnetic bar for about half hour before adding 20 ml distilled water. A clear solution was obtained.

The solution was then spray dried with a BUCHI Mini B-290 spray dryer at 140° C. with the liquid feed rate at 2.5 ml/min. A white free flowing powder was obtained.

10 mg powder was dispersed into 10 ml distilled water, giving a crystal clear nanodispersion with a particle size of 86 nm.

Example 23

0.10 g Irbesartan, 0.20 g PVP k30, 0.20 g HPC, and 0.50 g HPMC were all dispersed into 25 ml absolute ethanol followed by addition of 25 ml acetone. The suspension was stirred intensively with a magnetic bar for about half hour before adding 20 ml distilled water. A clear solution was obtained.

The solution was then spray dried with a BUCHI Mini B-290 spray dryer at 140° C. with the liquid feed rate at 2.5 ml/min. A white free flowing powder was obtained.

10 mg powder was dispersed into 10 ml distilled water, giving a crystal clear nanodispersion with a particle size of 227 nm.

Example 24

0.10 g Irbesartan, 0.20 g PVP k30, 0.20 g HPC, 0.20 g HPMC, and 0.30 g PEG 6000 were all dispersed into 25 ml absolute ethanol followed by addition of 25 ml acetone. The suspension was stirred intensively with a magnetic bar for about half hour before adding 20 ml distilled water. A clear solution was obtained.

The solution was then spray dried with a BUCHI Mini B-290 spray dryer at 140° C. with the liquid feed rate at 2.5 ml/min. A white free flowing powder was obtained.

10 mg powder was dispersed into 10 ml distilled water, giving a crystal clear nanodispersion with a particle size of 155 nm.

Example 25

0.10 g Irbesartan, 0.20 g PVP k30, 0.50 g HPC, and 0.20 g HPMC were all dispersed into 25 ml absolute ethanol followed by addition of 25 ml acetone. The suspension was stirred intensively with magnetic bar for about half hour before adding 20 ml distilled water. A clear solution was obtained. The solution was then spray dried with a BUCHI Mini B-290 spray dryer at 190° C. with the liquid feed rate at 2.5 ml/min. A white free flowing powder was obtained.

10 mg powder was dispersed into 10 ml distilled water, giving a crystal clear nanodispersion with a particle size of 81 nm.

Example 26

0.10 g Irbesartan, 0.20 g PVP k30, 0.20 g HPC, 0.20 g HPMC, and 0.30 g PEG 6000 were all dispersed into 25 ml absolute ethanol followed by addition of 25 ml acetone. The suspension was stirred intensively with a magnetic bar for about half hour before adding 20 ml distilled water. A clear solution was obtained.

The solution was then spray dried with a BUCHI Mini B-290 spray dryer at 190° C. with the liquid feed rate at 2.5 ml/min. A white free flowing powder was obtained.

10 mg powder was dispersed into 10 ml distilled water, giving a crystal clear nanodispersion with a particle size of 165 nm.

Example 27

0.30 g Irbesartan, 0.20 g PVP k30, 0.30 g HPC, and 0.20 g HPMC were all dispersed into 25 ml absolute ethanol followed by addition of 25 ml acetone. The suspension was stirred intensively with a magnetic bar for about half hour before adding 20 ml distilled water. A clear solution was obtained.

The solution was then spray dried with a BUCHI Mini B-290 spray dryer at 190° C. with the liquid feed rate at 2.5 ml/min. A white free flowing powder was obtained.

10 mg powder was dispersed into 10 ml distilled water, giving a translucent nanodispersion with a particle size of 779 nm.

The invention claimed is:

1. A process for the production of a non-porous, solid, water-soluble composition comprising a water-insoluble sartan, wherein the water-insoluble sartan has a solubility in water of less than 10 g/L, which comprises the steps of:
   a) providing an emulsion consisting essentially of:
      i) a solution of the water-insoluble sartan in a water-immiscible solvent for the same, and
      ii) an aqueous solution of a water-soluble carrier material, wherein the water-soluble carrier material consists essentially of at least one surfactant and at least one polymer, and,
   b) spray-drying the emulsion to remove water and the water-immiscible solvent to obtain a substantially solvent-free nano-dispersion of the water-insoluble sartan in the water-soluble carrier material.

2. A process for the production of a non-porous, solid, water-soluble composition comprising a water-insoluble sartan, wherein the water-insoluble sartan has a solubility in water of less than 10 g/L, which comprises the steps of:
   a) providing a single phase mixture consisting essentially of:
      i) at least one non-aqueous solvent,
      ii) optionally, water
      iii) a water-soluble carrier material soluble in the mixture of (i) and (ii), wherein the water-soluble carrier material consists essentially of at least one surfactant and at least one polymer, and
      iv) the water-insoluble sartan which is soluble in the mixture of (i) and (ii), and,
   b) spray-drying the solution to remove water and the water miscible solvent to obtain a substantially solvent-free nano-dispersion of the water-insoluble sartan in the water-soluble carrier material.

3. The process according to claim 1, wherein the spray drying process is conducted at a temperature at or above 120 Celsius.

4. The process according to claim 1, wherein the at least one polymer of the water-soluble carrier material is selected from the group consisting of polyethylene glycol, polyvinylpyrrolidone, poly(2-ethyl-2-oxazaline), polyvinyl alcohol, hydroxypropyl cellulose and hydroxypropyl-methyl cellulose and alginate.

5. The process according to claim 1, wherein the at least one surfactant of the water-soluble carrier material is selected from the group consisting of alkoxylated non-ionic surfactant, ether sulphate surfactant, cationic surfactant or ester surfactant.

6. The process according to claim 1, wherein the non-aqueous solvent includes at least one of dichloromethane, chloroform, ethanol, acetone and dimethyl sulphoxide.

7. The process according to claim 2, wherein the spray drying process is conducted at a temperature at or above 120 Celsius.

8. The process according to claim 2, wherein the at least one polymer of the water-soluble carrier material is selected from the group consisting of polyethylene glycol, polyvinylpyrrolidone, poly(2-ethyl-2-oxazaline), polyvinyl alcohol, hydroxypropyl cellulose and hydroxypropyl-methyl cellulose and alginate.

9. The process according to claim 2, wherein the at least one surfactant of the water-soluble carrier material is selected from the group consisting of alkoxylated non-ionic surfactant, ether sulphate surfactant, cationic surfactant or ester surfactant.

10. The process according to claim 2, wherein the non-aqueous solvent includes at least one of dichloromethane, chloroform, ethanol, acetone and dimethyl sulphoxide.

* * * * *